(12) United States Patent
Graeber

(10) Patent No.: US 7,642,288 B2
(45) Date of Patent: *Jan. 5, 2010

(54) TOPICAL APPLICATION OF ADAPALENE FOR THE LONG-TERM TREATMENT OF ACNE VULGARIS

(75) Inventor: Michael Graeber, Lawrenceville, NJ (US)

(73) Assignee: Galderma Research & Development, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/878,736

(22) Filed: Jul. 26, 2007

(65) Prior Publication Data

US 2008/0064755 A1    Mar. 13, 2008

Related U.S. Application Data

(63) Continuation of application No. PCT/EP2006/001140, filed on Jan. 23, 2006.

(60) Provisional application No. 60/647,306, filed on Jan. 26, 2005.

(51) Int. Cl.
| | |
|---|---|
| *A01N 37/10* | (2006.01) |
| *A01N 31/04* | (2006.01) |
| *A61K 31/19* | (2006.01) |
| *A61K 31/07* | (2006.01) |

(52) U.S. Cl. ..................................... 514/569; 514/725
(58) Field of Classification Search .................. 514/569
See application file for complete search history.

(56) References Cited

U.S. PATENT DOCUMENTS 4,717,720 A * 1/1988 Shroot et al. .................. 514/63

OTHER PUBLICATIONS

Differin-Adapalene Data Sheet. As of Nov. 1998, pp. 1-5.*
Cassano et al., "Studio multicentrico in aperto sul trattamento dell'acne lieve/moderata con adapalene in monoterapia o in terapia combinata" (English Translation: "Treatment of Mild to Moderate Acne Vulgaris With Adapalene Alone or Combined with Other Anti-Acne Agents. A Multicenter Open Trial."), G Ital Dermatol Venereol, 2002: 137:369-75 (includes extensive English-language summary).
International Search Report for PCT/EP2006/001140, dated May 18, 2006.

* cited by examiner

*Primary Examiner*—Sreeni Padmanabhan
*Assistant Examiner*—Samira Jean-Louis
(74) *Attorney, Agent, or Firm*—Buchanan, Ingersoll & Rooney P.C.

(57) ABSTRACT

Administration of adapalene in a topical medicament to a patient so as to sustain its biological response in the treatment of acne vulgaris, wherein the administration pattern of the topical medicament comprises topically applying onto the afflicted skin area a therapeutically effective amount of adapalene at least once every two days for at least 6 months.

9 Claims, 1 Drawing Sheet

TOPICAL APPLICATION OF ADAPALENE FOR THE LONG-TERM TREATMENT OF ACNE VULGARIS

CROSS-REFERENCE TO PRIORITY/PROVISIONAL APPLICATIONS

This application claims priority under 35 U.S.C. § 119 of U.S. Application No. 60/647,306, filed Jan. 26, 2005, and is a continuation of PCT/EP 2006/001140, filed Jan. 23, 2006, and designating the United States, published in the English language as WO 2006/079563 A1 on Aug. 3, 2006, each hereby expressly incorporated by reference in its entirety and each assigned to the assignee hereof.

BACKGROUND OF THE INVENTION

1. Technical Field of the Invention

The present invention relates to a regimen for the long-term treatment of acne vulgaris.

2. Description of Background and/or Related and/or Prior Art

Acne vulgaris is a common skin disorder that accounts for up to 20% of the visits to a dermatology facility, and affects the majority of the teenage population. Management of acne is challenging, especially when considering the chronicity of the disease and its variability in response to treatment.

The management of acne often requires combination therapy and a long-term therapeutic strategy. (See, for example, Thiboutot D., "New treatments and therapeutic strategies for acne," *Arch. Family. Med.*, 2000; 9: 179-187; Gollnick H, Cunliffe W, Berson D, et al., "Management of acne, a report from a Global Alliance to Improve Outcomes in Acne," *J. Am. Acad. Dermatol.*, 2003;49(I suppl):SI-S37). Maintenance therapy is necessary for many acne patients, as acne lesions have been shown to recur after. discontinuing a successful treatment regimen. (See Gollnick H, Cunliffe W, Berson D, et al., "Management of acne, a report from a Global Alliance to Improve Outcomes in Acne," *J. Am. Acad. Dermatol.*, 2003;49(I suppl):SI-S37; Thielitz A, Helmdach M, Ropke E-M, Gollnick H., "Lipid analysis of follicular casts from cyanoacrylate strips as a new method for studying therapeutic effects of anti-acne agents," *Br. J. Dermatol.*, 2001; 145:19-27).

Despite the variety of medications available for the treatment of acute acne, there are few studies with respect to the safety and efficacy of the long-term treatment of patients with acne vulgaris.

Currently, the most effective comedolytic agents are oral isotretinoin and topical retinoids. (See Cunliffe W J, Holland D B, Clark S M, Stables, G I, "Comedogenesis: some new aetiological, clinical and therapeutic strategies," *Br. J. Dermatol.*, 2000; 142: 1084-1091). Oral isotretinoin is an impractical choice for long-term therapy due to the potential for toxicity and teratogenicity. Topical anti-acne medication such as retinoids, could be associated with elevated skin irritation, so careful consideration must be given to the tolerability of a potential maintenance therapy. Cutaneous side effects may decrease the likelihood of treatment adherence, particularly when treating an asymptomatic condition. (See Koo J., "How do you foster medication adherence for better acne vulgaris management?" *SKINmed.*, 2003; 2:229-33; and Haider A, Shaw J C., "Treatment of acne vulgaris," *JAMA.*, 2004;292: 726-735).

Adapalene (6-[3-(1-adamantyl)-4-methoxyphenyl]-2-naphthoic acid) is a naphthoic acid derivative with potent retinoid and anti-inflammatory properties. Adapalene was developed for the topical treatment of acne vulgaris and other retinoid-sensitive dermatoses including various disorders of keratinization, proliferation and differentiation. Adapalene acts mainly by regulating differentiation of keratinocytes (comedolytic effect and preventing new comedones), but also has anti-inflammatory activity.

Reported non-serious adverse reactions associated with adapalene include common signs and symptoms of local irritative reactions (erythema, peeling, dry skin, pruritus, burning and stinging), rare cases of local allergic reactions (edema at the application site, contact eczema or dermatitis), or other skin and appendage disorders (very rare cases of hypopigmentation and hyperpigmentation, photosensitivity reactions, hair thinning, hair growth, skin erosion following facial waxing).

However, adapalene and other effective retinoids were studied in short-term (usually 12 weeks) clinical trials. Therefore, need exists to develop a safe and effective method of long-term treatment of acne vulgaris.

SUMMARY OF THE INVENTION

The present invention provides an effective method of treating acne vulgaris on a long-term basis via the administration of adapalene.

The present invention thus provides a long-term treatment of acne vulgaris with superior efficacy and comparable tolerability by administering higher strengths of adapalene as compared to short-term studies.

Generally, this invention features the formulation of adapalene in the preparation of a topical medicament for administering to a patient to sustain its biological response in the treatment of acne vulgaris, wherein the administration pattern of the topical medicament comprises administering a therapeutically effective amount of adapalene at least once every two days for at least 6 months, preferably once daily for at least 6 months, more preferably once daily for at least 12 months. Note: The protocol mandated 12 month once daily treatment according to clinical need.

Preferably, the topical medicament is applied to the afflicted skin for at least 6 months, preferably for at least 9 months and more preferably for at least 12 months. The invention also features a regimen for treating a patient afflicted with acne vulgaris comprising topically applying to the afflicted skin region of the patient a topical medicament (which is here a dermatological preparation) which comprises a therapeutically effective amount of adapalene at least once every two days, preferably once daily for at least 6 months, more preferably once daily for at least 12 months.

The topical medicament, which is a dermatological preparation, can be applied to the afflicted skin region in the evening after wash, preferably once daily. Preferably, the dermatological preparation is an aqueous gel composition comprising a higher strength, i.e., at least 0.2%, more preferably 0.25% to 0.5%, most preferably 0.3% by weight of adapalene.

More specifically, the present invention features formulation of adapalene in the preparation of a topical medicament for administering to a patient so as to sustain its biological response in the treatment of acne vulgaris, wherein the administration pattern of the topical medicament comprises administering 0.3% by weight of adapalene once daily for at least 3 months, preferably 6, more preferably 12 months. This invention also features a regimen for the long-term treatment of acne vulgaris comprising topically applying to the afflicted skin of a patient a topical medicament comprising 0.3% by weight of adapalene once daily for at least 3 months, preferably 6, more preferably 12 months.

Preferably, the topical medicament is a gel composition comprising 0.3% by weight of adapalene and is applied to the afflicted skin for at least 9 months, preferably for at least 12 months. The topical medicament is particularly efficient when the afflicted skin contains 20 to 100 non-inflammatory lesions, 20 to 50 inflammatory lesions, and no active nodules or cysts. For a more complete description of the invention, its operating advantages, and specific aspects attained by its use, reference should be had to the drawings and descriptive matter in which there are illustrated and described preferred embodiments of the invention.

Figure 1:
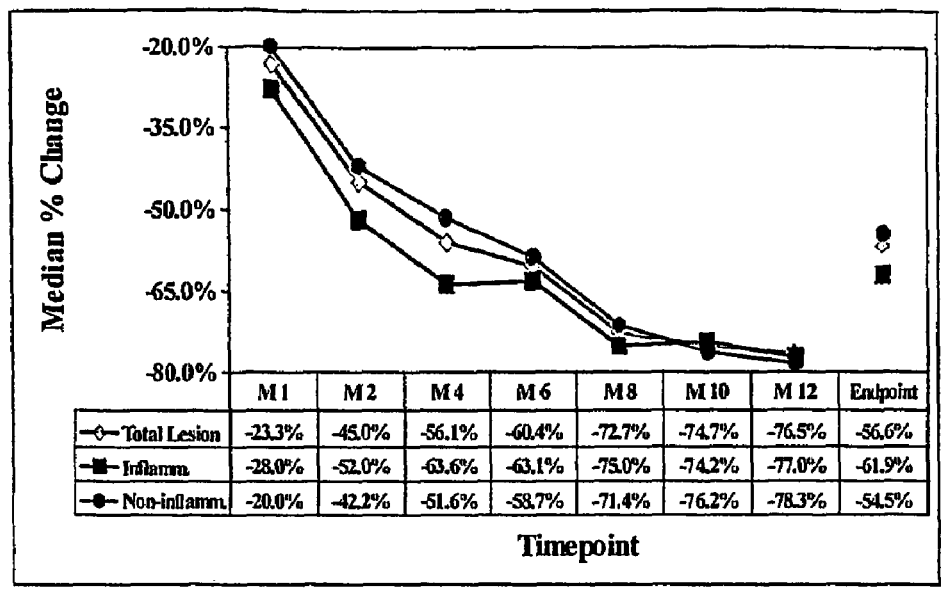
FIG. 1 is a graph showing time course of median percentage change in lesion counts.

DETAILED DESCRIPTION OF BEST MODE AND SPECIFIC/PREFERRED EMBODIMENTS OF THE INVENTION

The present invention features a method for the long term treatment of acne vulgaris by administration of a gel composition containing 0.3% by weight of adapalene. Such product has the following composition:

| Aqueous Gel: | |
| --- | --- |
| Adapalene | 3 mg |
| Carbomer 940 (BF Goodrich Carbopol 980) | 11 mg |
| Disodium Edetate | 1 mg |
| Methyl paraben | 2 mg |
| Poloxamer 124 | 2 mg |
| Propylene glycol | 40 mg |
| Sodium hydroxide: amount required to obtain a pH 5.0 ± 0.3 | |
| Purified water | q.s. 1 g |

The following details a study that clearly demonstrates the clinical benefit of long-term treatment of acne with adapalene gel 0.3%.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE

Clinical Test of Long Term Treatment of Acne Vulgaris with a Gel Composition Containing 0.3% by Weight of Adapalene Methods:

Study Design and Subjects:

This was a multi-center, open-label study of the long-term (up to 12 months) safety of Adapalene Gel, 0.3% applied once daily in subjects aged 12 years and older with acne vulgaris. The primary objective was to assess safety and the secondary objective was to assess efficacy. Subjects gave written, informed consent before undergoing any study procedure. Subjects were male and female (demonstrably non-gravid and either infertile or using appropriate forms of birth control), with at least 20-50 inflammatory lesions (no active nodules or cysts) and 20-100 non-inflammatory lesions. Qualified subjects (n=551) were enrolled at 20 independent centers in the United States and instructed to apply Adapalene Gel, 0.3% once daily to the face and trunk (if applicable) for a period of 12 months. Subjects were evaluated at Baseline, Week 1, and Months 1, 2, 4, 6, 8, 10 and 12 (or Early Termination Visit).

Expected signs and symptoms of local tolerability (cutaneous irritation) were evaluated at each visit: erythema, scaling, dryness, and stinging/burning (all rated on a scale ranging from 0 [none] to 3 [severe]). Adverse events and routine laboratory parameters (hematology, chemistry, and urinalysis) were recorded throughout the study. Efficacy data were summarized for percent changes from Baseline (in non-inflammatory, inflammatory and total lesion counts) and the subject's assessment of acne (i.e., assessment of improvement at months 6 and 12).

Of the 551 subjects enrolled, fifty point one percent of subjects were male, mean age was 18.9 years, and 72.4% were Caucasian, 12.5% Black, 12.5% Hispanic, 0.5% Asian, and 2.0% other races. Most subjects had oily skin (63.9%). Skin Phototype III was the most common (35.2%).

This study was conducted in accordance with the ethical principles outlined in the Declaration of Helsinki and Good Clinical Practice (GCP), and in compliance with local regulatory requirements. All subjects in this study gave written, informed consent to participate before any study procedures were initiated. Subjects 18 years of age and older signed the informed consent; subjects under 18 years signed an assent to participate and the parent or guardian signed the informed consent.

Efficacy and Safety Variables:

Table 1 is a flow chart of assessed measurements during this study.

TABLE 1

FLOW CHART OF EFFICACY AND SAFETY MEASUREMENTS

| Parameter | Screening | Baseline | Wk 1 | Months 1, 2 & 4 | Month 6 | Month 8 | Month 10 | Month 12/ Early Termination Visit |
| --- | --- | --- | --- | --- | --- | --- | --- | --- |
| | | | | Efficacy | | | | |
| Lesion Counts | | X | | X | X | X | X | X |
| Subject's | | | | | X | | | X |

TABLE 1-continued

FLOW CHART OF EFFICACY AND SAFETY MEASUREMENTS

| Parameter | Screening | Baseline | Wk 1 | Months 1, 2 & 4 | Month 6 | Month 8 | Month 10 | Month 12/ Early Termination Visit |
|---|---|---|---|---|---|---|---|---|
| Assessment of Acne | | | | | | | | |
| Oiliness (facial) | | X | | | X | | | X |
| Safety | | | | | | | | |
| Local Tolerability | | X | X | X | X | X | X | X |
| Adverse Events | X | X | X | X | X | X | X | X |
| Blood and Urine Sampling | X | | | | X | | | X |

Wk = Week
M = Month

The Investigator (or responsible designee) conducted efficacy evaluations consisting of non-inflammatory lesion counts (open and closed comedones) and inflammatory lesion counts (papules and pustules) and nodules/cysts. Lesion counts were taken from the face only. Subject's assessment of acne was also documented.

Non-inflammatory and inflammatory lesions were counted on the forehead, left and right cheeks, and chin above the jaw line (excluding the nose). Total lesion counts were calculated by the Sponsor. The following definitions were used:

Non-Inflammatory Lesions:
  Open Comedone: A mass of sebaceous material that is impacted behind an open follicular orifice (blackhead).
  Closed Comedone: A mass of sebaceous material that is impacted behind a closed follicular orifice (whitehead).
Inflammatory Lesions:
  Papule: A small, solid elevation less than one centimeter in diameter.
  Pustule: A small, circumscribed elevation of the skin that contains yellow-white exudate.
Nodule/Cyst:
  A circumscribed, elevated lesion generally more than 1.0 cm in diameter.

Subjects evaluated their facial acne at the Month 6 and Month 12/Early Termination Visit, as compared to the Baseline Visit, according to the following scale:

TABLE 2

| | |
|---|---|
| 1 | Marked Improvement |
| 2 | Moderate Improvement |
| 3 | Minimal Improvement |
| 4 | No Change |
| 5 | Worse |

The safety variables evaluated were: local tolerability (erythema, scaling, dryness, and stinging/burning), Adverse Events (AEs), and routine laboratory data (hematology, blood chemistry, and urinalysis). Side effects expected during treatment with topical retinoids include erythema, scaling, dryness, and stinging/burning. During the study, the course of these expected events was assessed as local tolerability.

Erythema, scaling, dryness, and stinging/burning were rated on the following scales:

TABLE 3

Erythema: abnormal redness of the skin.

| None | 0 | No erythema |
|---|---|---|
| Mild | 1 | Slight pinkness present |
| Moderate | 2 | Definite redness, easily recognized |
| Severe | 3 | Intense redness |

TABLE 4

Scaling: abnormal shedding of the stratum corneum.

| None | 0 | No scaling |
|---|---|---|
| Mild | 1 | Barely perceptible shedding, noticeable only on light scratching or rubbing |
| Moderate | 2 | Obvious but not profuse shedding |
| Severe | 3 | Heavy scale production |

TABLE 5

Dryness: brittle and/or tight sensation.

| None | 0 | No dryness |
|---|---|---|
| Mild | 1 | Slight but definite roughness |
| Moderate | 2 | Moderate roughness |
| Severe | 3 | Marked roughness |

TABLE 6

Stinging/Burning: prickling pain sensation immediately after (within 5 minutes of) dosing.

| None | 0 | No stinging/burning |
|---|---|---|
| Mild | 1 | Slight warm, tingling/stinging sensation; not really bothersome |
| Moderate | 2 | Definite warm, tingling/stinging sensation that is somewhat bothersome |
| Severe | 3 | Hot, tingling/stinging sensation that has caused definite discomfort |

Erythema, scaling, and dryness were evaluated by the Investigator. Stinging/burning was recorded by the Investigator after discussion with the subject.

Local tolerability measures of the signs and symptoms of skin irritation were considered adverse effects only if the severity of the expected signs and symptoms was such that an interruption of the subject's participation in the study, at his/her request or at the Investigator's discretion, had occurred. Altered dosing regimens (such as every other day dosing) to manage irritation were not considered to be an interruption of the subject's participation in the study.

Adverse Events (AEs):

An AE was defined as any unfavorable and unintended sign (e.g., including a clinically relevant abnormal laboratory finding), symptom, or disease temporally associated with the use of a medicinal (investigational) product, whether or not related to the investigational product. Any new sign, symptom or disease, or clinically significant increase in the intensity of an existing sign, symptom or disease, was considered an AE. This included any new signs or symptoms suffered by the subject after accidental or intentional overdose or misuse. Lack of efficacy of the study drug was not considered an AE unless it led to other unfavorable medical occurrences. However, clinically significant worsening of the treated disease was considered an AE. Pregnancy was not considered an AE but was an important medical event.

Severity of an AE was rated as mild, moderate, or severe. Relationship of an AE to study drug was rated as: related (possibly, probably or definitely related) or unrelated (unlikely or definitely unrelated).

Serious Adverse Events (SAEs):

An SAE was defined as any untoward medical occurrence that at any dose:

Resulted in death

Was life-threatening (i.e., the subject was at risk of death at the time of the event, but not an event which hypothetically might have caused death if it were more severe)

Required inpatient hospitalization or prolongation of an existing hospitalization (hospitalization solely for diagnostic tests, even if related to an adverse event, elective hospitalization for any intervention planned before subject entered the study, or admission to a day-care facility did not themselves constitute an SAE)

Resulted in persistent or significant disability/incapacity

Was a congenital anomaly/birth defect, or

Was any other important medical event that jeopardized the subject or required intervention to prevent one of the outcomes listed above.

Routine Laboratory Tests:

Blood and urine samples were obtained according to the schedule specified in the study flow chart of Table 1. The following blood chemistries were evaluated: protein, albumin, globulin, A/G ratio, bilirubin (total), alanine transaminase (ALT), aspartate transaminase (AST), alkaline phosphate, GGT, lactic dehydrogenase (LDH), urea nitrogen, creatinine, uric acid, cholesterol (total), triglycerides, and glucose.

The following hematology parameters were evaluated: hematocrit, hemoglobin, red cell count, mean corpuscular volume (MCV), mean corpuscular hemoglobin (MCH), mean corpuscular hemoglobin concentration (MCHC), white cell count, and platelet count.

A routine urinalysis for the following was performed: color, appearance, specific gravity, urine reaction pH, glucose, protein (qualitative.), ketones, occult blood, bilirubin, nitrite, and leukocytes.

Other Assessment:

Facial Oiliness, an additional measure, was rated by the investigator on the following scale:

TABLE 7

| None | 0 | No oiliness |
|---|---|---|
| Mild | 1 | Slight but definite greasiness |
| Moderate | 2 | Moderate greasiness |
| Severe | 3 | Marked greasiness |

Appropriateness of Measurements:

Efficacy was evaluated by lesion counting which is a current practice to assess improvement of acne.

Safety measures were based on the known profile of retinoids and standard procedures for reporting safety (AEs and laboratory values) in clinical research.

Statistical Analyses:

As this was an open-label study, only descriptive data presentations were made. No formal statistical hypotheses were tested. Descriptive statistics were used to summarize all data. For continuous variables, the number of subjects (N), mean, standard deviation (SD), median, minimum and maximum are provided for the data collected at each visit and the changes/percent changes from baseline at each post-baseline visit. For categorical variables, frequencies and percentages for each category are provided.

All summaries for subject characteristics and efficacy data were based on the Intent to Treat (ITT) population (this population consisted of all subjects enrolled, to whom study medication was dispensed). All safety data is based on the safety population (all subjects who applied study drug at least once).

Analysis visits were imputed according to an algorithm to summarize data by the treatment duration. If multiple measurements were present within the same interval, the measurement closest to the target study day was used for analysis. If two measurements were taken with equal differences in timing compared with the target day, data from the nominal visit number (recorded on the case report form) was used for analysis. For example, if measurements were collected on Day 360 and Day 367, the data collected at Day 360 was used for analysis at Month 12 while data collected at Day 367 was used in analysis for endpoint. Although all data were used in imputing the visits for analysis, some data were not used for analysis due to multiple observations within a visit window.

Subject data for all treated subjects were summarized by four quarters of the study: "Baseline to <3 months", "3 months to <6 months", "6 months to <9 months", and "9 months to 1 year." The number of subjects at risk for each period (i.e. subjects available at beginning of each period) was tabulated. The number of subjects at risk is determined based on each subject's treatment duration. Each month was considered to be 30 days for these calculations, and a 7-day visit window was used. Thus, "Baseline to <3 months" is Day 1 through Day 82, "3 months to <6 months" is Day 83 through Day 172, "6 months to <9 months" is Day 173 through Day 262, "9 months to <1 year" is Day 263 through Day 352, and "1 year and above" is Day 353 and above.

By the same principle, subject completion/discontinuation was summarized by subjects and by four quarters. The discontinuation rate for each quarter was calculated by the number of subjects who discontinued within the period divided by the number of subjects at risk for the given period.

Safety Analyses:

Local Tolerability Assessment:

Local tolerability variables (erythema, scaling, dryness, and stinging/burning) were summarized by a severity score on a 4-point scale at each visit (0=none to 3=severe). Each subject's "Worst" score and the "Final"

score were summarized where "Worst" was the highest score and "Final" was the last observation during the post-baseline period.

The number of subjects whose local tolerability data were worse (higher score) than their Baseline score was tabulated at each post-baseline visit. The "Worst" and "Final" scores for each subject, if higher than Baseline were tabulated.

Adverse Events:

All AEs recorded on the case report forms (CRFs) are displayed in data listings.

AEs were also summarized for all subjects. A subject was counted only once per body system, even if more than one event was reported, and only once per COSTART (Coding Symbols for Thesaurus of Adverse Reaction Terms), even if more than one occurrence was reported.

The AE incidence by quarter was summarized for "Baseline to <3 months", "3 months to <6 months", "6 months to <9 months", and "9 months to 1 year." The AE incidence for each period was calculated as the number of subjects with AE onset dates within the period divided by the number of subjects at risk per period.

AE summary tables are listed in the Statistical Analysis Plan (SAP).

Laboratory Data:

Descriptive statistics for each laboratory parameter are provided for data collected at each visit and for the changes from Screening at each post-baseline visit. "Final" was imputed by the last observation during the post-baseline period.

A shift table for the laboratory data at Screening versus Final assessment was constructed for laboratory parameters for which numeric reference ranges were available. The number of subjects below, within, and above the laboratory reference ranges at Screening versus the Final assessment was summarized.

For each laboratory test, a complete data listing is provided for subjects who have any laboratory results outside the reference ranges.

Laboratory result assessments of clinical significance or clinical non-significance by investigators recorded on the CRF page were tabulated with a supporting data listing.

Efficacy Analyses:

Counts of the three lesion types (non-inflammatory, inflammatory, and total) were summarized at each visit and change and percent change from baseline at each post-baseline visit. The observed data at each visit and at Endpoint were summarized, where Endpoint was considered the last available data point during the treatment period (last value carried forward), including Baseline if no post-Baseline data were available. Subgroup summaries for the lesion data are provided by gender (male vs. female), race (Caucasian vs. non-Caucasian) and age group (<18, 18 to 64). Subject's assessment of acne and facial oiliness were summarized as categorical variables by visit and endpoint.

Results:

Subject Disposition and Baseline Characteristics:

Five hundred fifty-one (551) subjects were enrolled at 20 study centers in the United States. Table 8 provides a summary of subject enrollment. Of the 551 subjects enrolled, 362 (65.7%) were treated for 3 months or more, 303 (55.0%) were treated for 6 months or more, and 166 (30.1%) were treated for at least 1 year (>353 days).

TABLE 8

Summary of Subject Enrollment And At Risk

| Disposition | Adapalene Gel, 0.3% (N = 551) | |
|---|---|---|
| | n* | % |
| Baseline to <Month 3 (1 to <83 days) | 551 | 100.0 |
| Month 3 to <Month 6 (83 to <173 days) | 362 | 65.7 |
| Month 6 to <Month 9 (173 to <263 days) | 303 | 55.0 |
| Month 9 to <1 Year (263 to <353 days) | 174 | 31.6 |
| ≧1 Year (≧353 days) | 166† | 30.1 |

*All N's reported indicate the total number of subjects exposed to drug at the beginning of the specified study period.
†One hundred sixty-seven (167) subjects completed all study visits; however, one subject was not included since all visits were completed in 342 days, outside the window for the 12-month analysis.

Of the 551 enrolled subjects, 384 (69.7%) did not complete 12 months of treatment. The two most frequent reasons for discontinuation were administrative actions: 93 (16.9%) subjects discontinued due to "Sponsor's decision" and 126 (22.9%) subjects discontinued due to "site closing."

Seventy (12.7%) subjects discontinued due to "lost to follow-up". As defined within the study protocol, this category was to be used only after the study site personnel tried twice to reach the subject by telephone plus a letter without answer. The number of subjects who were lost to follow-up is consistent with the expected attrition rate for a study population consisting of young, healthy subjects who are treating a non-life-threatening disease (acne vulgaris).

Fifteen (2.7%) subjects were discontinued from the study due to an AE; 11 (2.0%) of these occurred in the first 3 months of the study. Regardless of the reason for discontinuation, data from all subjects were included in the data summaries.

A summary of demographic and baseline characteristics is in Table 9. In total, 50.1% of the subjects were male, mean age was 18.9 years (age range of 11-52 years), and the majority, 72.4%, were Caucasian. Most subjects had oily skin (63.9%). Skin Phototype III was the most common (35.2%).

TABLE 9

DEMOGRAPHIC AND BASELINE CHARACTERISTICS
DEMOGRAPHICS - GENDER, RACE, SKIN TYPE, AGE, SKIN PHOTOTYPE

| | | Adapalene Gel 0.3% (N = 551) |
|---|---|---|
| Gender | | |
| Male | n (%) | 276 (50.1) |
| Female | n (%) | 275 (49.9) |
| Race | | |
| White | n (%) | 399 (72.4) |
| Black | n (%) | 69 (12.5) |
| Asian | n (%) | 3 (0.5) |
| Hispanic | n (%) | 69 (12.5) |
| Other | n (%) | 11 (2.0) |
| Skin Type | | |
| Dry | n (%) | 10 (1.8) |
| Normal | n (%) | 175 (31.8) |
| Oily | n (%) | 352 (63.9) |
| Oily + Normal | n (%) | 5 (0.9) |
| Oily + Dry | n (%) | 9 (1.6%) |
| Age (years) | | |
| Mean | | 18.9 |
| S.D. | | 6.99 |

TABLE 9-continued

DEMOGRAPHIC AND BASELINE CHARACTERISTICS
DEMOGRAPHICS - GENDER, RACE, SKIN TYPE, AGE,
SKIN PHOTOTYPE

|  |  | Adapalene Gel 0.3%<br>(N = 551) |
|---|---|---|
| Median |  | 16.0 |
| Min, Max |  | 11, 52 |
| <12 | n (%) | 1 (0.2) |
| 12-17 | n (%) | 332 (60.3) |
| 18-64 | n (%) | 218 (39.6) |
| Skin Phototype |  |  |
| I | n (%) | 29 (5.3) |
| II | n (%) | 93 (16.9) |
| III | n (%) | 194 (35.2) |
| IV | n (%) | 139 (25.2) |
| V | n (%) | 55 (10.0) |
| VI | n (%) | 41 (7.4) |

Efficacy evaluation:

Table 10 and FIG. 1 provide a summary of the median percent change in non-inflammatory, inflammatory, and total lesion counts.

TABLE 10

SUMMARY OF LESION COUNTS
Median Count at Baseline and Median % Change at Post-Baseline

| | ITT Population | | | | | |
|---|---|---|---|---|---|---|
|  | N | Total Lesion count | N | Inflammatory Lesion count | N | Non-Inflammatory Lesion count |
| Baseline Count | 547* | 70.0 | 551 | 26.0 | 551 | 40.0 |
| Month 1 Observed | 494 | −23.3% | 497 | −28.0% | 497 | −20.0% |
| Month 2 Observed | 476 | −45.0% | 479 | −52.0% | 479 | −42.2% |
| Month 4 Observed | 345 | −56.1% | 347 | −63.6% | 347 | −51.6% |
| Month 6 Observed | 310 | −60.4% | 312 | −63.1% | 312 | −58.7% |
| Month 8 Observed | 198 | −72.7% | 198 | −75.0% | 198 | −71.4% |
| Month 10 Observed | 169 | −74.7% | 169 | −74.2% | 169 | −76.2% |
| Month 12 Observed | 170 | −76.5% | 170 | −77.0% | 170 | −78.3% |
| Endpoint† | 547 | −56.6% | 551 | −61.9% | 551 | −54.5% |

*Four subjects had missing total lesion count data at baseline since nodule/cyst counts were not available.
†Endpoint = Last observation carried forward, including Baseline.

Treatment with Adapalene Gel, 0.3% for up to 12 months showed continuing improvement in lesion counts (non-inflammatory, inflammatory and total) starting at Month 1, the second post-Baseline visit at which lesion count was performed, until the end of the 12-month treatment. The greatest reductions in lesion counts were seen after 12 months of treatment and reached at least 75% reduction from baseline.

A summary of subject's assessment of acne is in Table 11. Overall improvement was observed in the subject's assessment of acne. The median assessment was "Moderate Improvement" at Month 6, and "Marked Improvement" at Month 12.

TABLE 11

SUBJECT'S ASSESSMENT OF ACNE

| | | Improvements | |
|---|---|---|---|
| Time point | Median assessment | Moderate (%) | Marked (%) |
| Month 6 (n = 313) | Moderate Improvement | 59.7 | 21.4 |
| Month 12 (n = 167*) | Marked Improvement | 34.1 | 55.7 |
| Endpoint (n = 462) | Moderate Improvement | 45.5 | 31.0 |

*Includes that subject who completed all the visits in 342 days.
Endpoint = Last observation carried forward, including baseline.

Ratings of facial oiliness were improved from Baseline at both Months 6 and 12. At Baseline, 69 (12.6%) subjects had no oiliness, versus 130 (41.7%) at Month 6 and 111 (66.1%) at Month 12.

Therefore, the following points were observed from this study:

Continuous reductions in non-inflammatory, inflammatory, and total lesion counts occurred over time.

Median reductions from baseline were greater than 75% for all lesion types by Month 12.

Safety Evaluation:

Extent of Exposure:

A total of 551 subjects received adapalene gel, 0.3% treatment in this study. The mean treatment duration was 190.2 days. The mean total amount of medication used was 141.24 grams (Range: 1.5-639.4 grams) per subject. The mean daily medication usage was 0.7 grams/day (Range: 0.02-6.7 grams/day) per subject. As used herein, daily medication usage (g/day)=total medication usage (g) divided by treatment duration (day).

Figure 2:
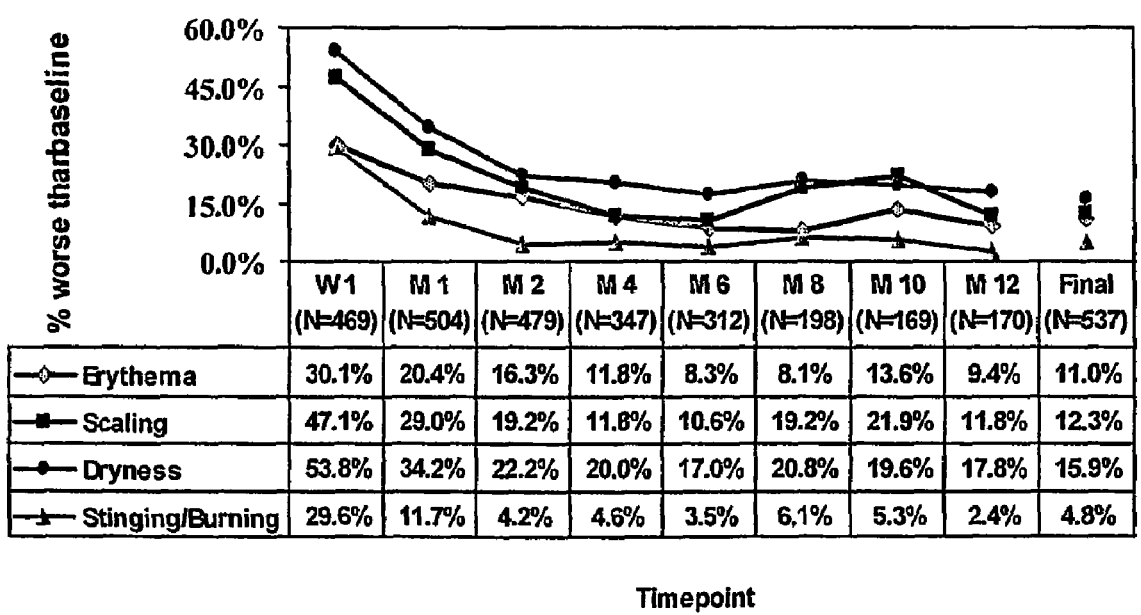
FIG. 2 is a graph showing time course of local cutaneous irritation (worse than baseline, observed data, and final score).

Local Tolerability:

Expected signs and symptoms of skin irritation (erythema, scaling, dryness and stinging/burning) were evaluated on a scale of 0 (none) to 3 (severe) at each visit. Table 12 and FIG. 2 present the percent of subjects with expected signs and symptoms of skin irritation worse than baseline.

TABLE 12

LOCAL CUTANEOUS IRRITATION* (WORSE THAN BASELINE)

|  | N | Erythema | N | Scaling | N | Dryness | N | Stinging/Burning |
|---|---|---|---|---|---|---|---|---|
| Week 1 (Observed) | 469 | 30.1% | 469 | 47.1% | 468 | 53.8% | 469 | 29.6% |
| Month 1 (Observed) | 504 | 20.4% | 503 | 29.0% | 503 | 34.2% | 504 | 11.7% |
| Month 2 (Observed) | 479 | 16.3% | 479 | 19.2% | 478 | 22.2% | 478 | 4.2% |
| Month 4 (Observed) | 347 | 11.8% | 347 | 11.8% | 345 | 20.0% | 347 | 4.6% |
| Month 6 (Observed) | 312 | 8.3% | 312 | 10.6% | 311 | 17.0% | 312 | 3.5% |
| Month 8 (Observed) | 198 | 8.1% | 198 | 19.2% | 197 | 20.8% | 198 | 6.1% |
| Month 10 (Observed) | 169 | 13.6% | 169 | 21.9% | 168 | 19.6% | 169 | 5.3% |
| Month 12 (Observed) | 170 | 9.4% | 170 | 11.8% | 169 | 17.8% | 170 | 2.4% |
| Final (Last score)† | 537 | 11.0% | 537 | 12.3% | 536 | 15.9% | 537 | 4.8% |
| Worst (Highest score)† | 537 | 45.4% | 537 | 60.7% | 536 | 67.5% | 537 | 38.4% |

*Local Cutaneous Irritation was reported as Local Cutaneous Tolerance; these terms are used interchangeably
†During the post-baseline period.
Percentages shown are subjects at each visit with scores worse than baseline.
Final: Last observation during post-Baseline period.
N = Number of subjects in the study with data available at Baseline and the specified timepoint (based on erythema)
Note:
Slight data point variations (±0.1%) in FIG. 2 are due to rounding rule effect.

The proportion of subjects for which there was a worsening from baseline in erythema, scaling, dryness and stinging/burning was greatest at Week 1 and declined continuously thereafter.

Expected signs and symptoms of local cutaneous irritation were mild to moderate in severity. Very few subjects had severe scores (Table 13).

TABLE 13

LOCAL CUTANEOUS IRRITATION* SCORES BY SEVERITY
(HIGHEST SCORES WORSE THAN BASELINE)

|  |  | Severity | | |
|---|---|---|---|---|
| Variable | N (%) N = 537† | Mild n (%) | Moderate n (%) | Severe n (%) |
| Erythema | 244 (45.4) | 170 (31.7) | 71 (13.2) | 3 (0.6) |
| Scaling | 326 (60.7) | 239 (44.5) | 84 (15.6) | 3 (0.6) |
| Dryness | 362 (67.5) | 277 (51.7) | 79 (14.7) | 6 (1.1) |
| Stinging/burning | 206 (38.4) | 155 (28.9) | 41 (7.6) | 10 (1.9) |

*Local Cutaneous Irritation was reported as Local Cutaneous Tolerance; these terms are used interchangeably
†N = 536 for dryness.

Adverse Events:

Of the 551 subjects enrolled, 244 (44.3%) had one or more AEs. Overall, 142 (25.8%) subjects reported one or more dermatologic AEs and 155 (28.1%) subjects reported one or more non-dermatologic AEs.

Serious AEs were reported by six subjects; all were non-related to study drug. There were no deaths in this study.

Discontinuation due to AEs occurred for 15 subjects (2.7%); all had dermatologic AEs and one had an additional non-dermatologic AE.

Drug-related AEs were reported by 119 subjects (21.6%); 117 subjects (21.2%) reported dermatologic, drug-related AEs.

The percent of subjects with severe AEs was 1.8% (10 subjects with 13 AEs). All were non-related to study drug. Only one event was dermatologic (one subject had an infected ingrown toenail).

The incidence of dermatologic AEs was highest in the first quarter [1 11 (20.1%) incidents] and decreased substantially by the second quarter [23 (6.4%) incidents] and remained low throughout the remainder of the study [18 (5.9%) and 10 (5.7%) for the third and fourth quarters, respectively]. Most of the dermatologic AEs were related to study drug and therefore the profile for AEs related to study drug followed the same profile for dermatologic AEs. Similarly, the majority of dermatologic AEs leading to discontinuation occurred in the first quarter.

The percent of subjects with non-dermatologic AEs was comparable between the first two quarters (first quarter: 13.1% and second quarter: 11.0%) and second two quarters (third quarter: 12.5% and fourth quarter: 17.2%). Drug-related non-dermatologic AEs were reported by four (0.7%) subjects (two with pain eye, one with headache and one with increased liver enzymes).

An overall summary of adverse events, most frequently reported adverse events, adverse events related to study drug, and incidence of adverse events coded as sunburn are displayed in Tables 14-17.

TABLE 14

Overall Summary Of Adverse Events

|  |  | Bsl to <3 Mo (N = 551) | Mo 3 to <Mo 6 (N = 362) | Mo 6 to <Mo 9 (N = 303) | Mo 9 to 1 Year (N = 174) | Total (N = 551) |
|---|---|---|---|---|---|---|
| Total Number of Adverse Events |  | 303 | 72 | 64 | 42 | 505 |
| Subjects who had any AE | n (%) | 161 (29.2) | 57 (15.7) | 48 (15.8) | 37 (21.3) | 244 (44.3) |
| Dermatologic | n (%) | 111 (20.1) | 23 (6.4) | 18 (5.9) | 10 (5.7) | 142 (25.8) |
| Non-dermatologic | n (%) | 72 (13.1) | 40 (11.0) | 38 (12.5) | 30 (17.2) | 155 (28.1) |

TABLE 14-continued

Overall Summary Of Adverse Events

|  |  | Bsl to <3 Mo (N = 551) | Mo 3 to <Mo 6 (N = 362) | Mo 6 to <Mo 9 (N = 303) | Mo 9 to 1 Year (N = 174) | Total (N = 551) |
|---|---|---|---|---|---|---|
| Subjects with AE related to study drug | n (%) | 98 (17.8) | 12 (3.3) | 13 (4.3) | 6 (3.4) | 119 (21.6) |
| Dermatologic | n (%) | 98 (17.8) | 10 (2.8) | 12 (4.0) | 6 (3.4) | 117 (21.2) |
| Non-dermatologic | n (%) | 1 (0.2) | 2 (0.6) | 1 (0.3) | 0 (0.0) | 4 (0.7) |
| Subjects with SAE | n (%) | 3 (0.5) | 1 (0.3) | 1 (0.3) | 1 (0.6) | 6 (1.1) |
| Dermatologic | n (%) | 0 (0.0) | 0 (0.0) | 0 (0.0) | 0 (0.0) | 0 (0.0) |
| Non-dermatologic | n (%) | 3 (0.5) | 1 (0.3) | 1 (0.3) | 1 (0.6) | 6 (1.1) |
| Subjects with AE leading to discontinuation | n (%) | 11 (2.0) | 3 (0.8) | 1 (0.3) | 0 (0.0) | 15 (2.7) |
| Dermatologic | n (%) | 11 (2.0) | 3 (0.8) | 1 (0.3) | 0 (0.0) | 15 (2.7) |
| Non-dermatologic | n (%) | 1 (0.2) | 0 (0.0) | 0 (0.0) | 0 (0.0) | 1 (0.2) |

Bsl = baseline
Mo = month
Note:
N's reflect the number of subjects at risk at the beginning of the time period.
Each subject was counted only once per AE row or body system row, regardless of the number of occurrences of the individual event or the number of AEs within the body system.

TABLE 15

MOST FREQUENTLY REPORTED (≧1%) ADVERSE EVENTS

|  |  | Adapalene Gel, 0.3% (N = 551) |
|---|---|---|
| Total No. of Subjects with Any AE | n (%) | 244 (44.3) |
| Skin and Appendages | n (%) | 142 (25.8) |
| Skin dry | n (%) | 59 (10.7) |
| Discomfort - skin | n (%) | 48 (8.7) |
| Sunburn | n (%) | 28 (5.1) |
| Desquamation | n (%) | 19 (3.4) |
| Erythema | n (%) | 16 (2.9) |
| Irritant Dermatitis | n (%) | 10 (1.8) |
| Pruritis | n (%) | 10 (1.8) |
| Dermatitis - contact | n (%) | 8 (1.5) |
| Body as a Whole | n (%) | 87 (15.8) |
| Flu syndrome | n (%) | 28 (5.1) |
| Injury - accidental | n (%) | 22 (4.0) |
| Lab test abnormal | n (%) | 14 (2.5) |
| Headache | n (%) | 12 (2.2) |
| Infection | n (%) | 6 (1.1) |
| Allergic Reaction | n (%) | 6 (1.1) |
| Respiratory System | n (%) | 48 (8.7) |
| Pharyngitis | n (%) | 28 (5.1) |
| Rhinitis | n (%) | 7 (1.3) |
| Sinusitis | n (%) | 6 (1.1) |
| Digestive System | n (%) | 25 (4.5) |
| Vomiting | n (%) | 6 (1.1) |
| Gastroenteritis | n (%) | 6 (1.1) |
| Special Senses | n (%) | 14 (2.5) |
| Otitis Media | n (%) | 7 (1.3) |
| Urogenital System | n (%) | 14 (2.5) |
| Nervous System | n (%) | 7 (1.3) |

Note:
N's reflect the number of subjects at risk throughout the study.
Each subject was counted only once per AE row or body system row, regardless of the number of occurrences of the individual or the number of AEs within the body system.

TABLE 16

DRUG RELATED ADVERSE EVENTS

|  |  | (BASE - <MO 3) (N = 551) | (Mo 3 - <Mo 6) (N = 362) | (Mo 6 - <Mo 9) (N = 303) | (Mo 9 - 1 Year) (N = 174) | Total (N = 551) |
|---|---|---|---|---|---|---|
| Total Number of AE(s) |  | 170 | 14 | 14 | 6 | 208 |
| Total Number (%) of Subjects with AE(s) | n (%) | 98 (17.8%) | 12 (3.3%) | 13 (4.3%) | 6 (3.4%) | 119 (21.6%) |
| Skin and Appendages | n (%) | 98 (17.8%) | 10 (2.8%) | 12 (4.0%) | 6 (3.4%) | 117 (21.2%) |
| Skin Dry | n (%) | 45 (8.2%) | 6 (1.7%) | 8 (2.6%) | 4 (2.3%) | 58 (10.5%) |
| Discomfort Skin | n (%) | 42 (7.6%) | 2 (0.6%) | 2 (0.7%) | 0 (0.0%) | 46 (8.3%) |
| Desquamation | n (%) | 14 (2.5%) | 2 (0.6%) | 1 (0.3%) | 0 (0.0%) | 18 (3.3%) |
| Sunburn | n (%) | 15 (2.7%) | 1 (0.3%) | 0 (0.0%) | 1 (0.6%) | 17 (3.1%) |
| Erythema | n (%) | 13 (2.4%) | 1 (0.3%) | 0 (0.0%) | 0 (0.0%) | 14 (2.5%) |
| Pruritus | n (%) | 8 (1.5%) | 0 (0.0%) | 0 (0.0%) | 1 (0.6%) | 10 (1.8%) |
| Irritant Dermatitis | n (%) | 9 (1.6%) | 0 (0.0%) | 0 (0.0%) | 0 (0.0%) | 9 (1.6%) |
| Seborrhea | n (%) | 1 (0.2%) | 0 (0.0%) | 1 (0.3%) | 0 (0.0%) | 2 (0.4%) |
| Dermatitis | n (%) | 1 (0.2%) | 0 (0.0%) | 1 (0.3%) | 0 (0.0%) | 2 (0.4%) |
| Edema Skin | n (%) | 2 (0.4%) | 0 (0.0%) | 0 (0.0%) | 0 (0.0%) | 2 (0.4%) |
| Skin Color | n (%) | 1 (0.2%) | 0 (0.0%) | 0 (0.0%) | 0 (0.0%) | 1 (0.2%) |
| Atopic Dermatitis | n (%) | 1 (0.2%) | 0 (0.0%) | 0 (0.0%) | 0 (0.0%) | 1 (0.2%) |

TABLE 16-continued

DRUG RELATED ADVERSE EVENTS

|  |  | (BASE - <M0 3) (N = 551) | (Mo 3 - <Mo 6) (N = 362) | (Mo 6 - <Mo 9) (N = 303) | (Mo 9 - 1 Year) (N = 174) | Total (N = 551) |
|---|---|---|---|---|---|---|
| Hirsutism | n (%) | 1 (0.2%) | 0 (0.0%) | 0 (0.0%) | 0 (0.0%) | 1 (0.2%) |
| Derm Contact | n (%) | 1 (0.2%) | 0 (0.0%) | 0 (0.0%) | 0 (0.0%) | 1 (0.2%) |
| Body as a Whole | n (%) | 0 (0.3%) | 1 (0.3%) | 1 (0.3%) | 0 (0.0%) | 2 (0.4%) |
| Lab Test Abnormality | n (%) | 0 (0.0%) | 0 (0.0%) | 1 (0.3%) | 0 (0.0%) | 1 (0.2%) |
| Headache | n (%) | 0 (0.0%) | 1 (0.3%) | 0 (0.0%) | 0 (0.0%) | 1 (0.2%) |
| Special Senses | n (%) | 1 (0.2%) | 1 (0.3%) | 0 (0.0%) | 0 (0.0%) | 2 (0.4%) |
| Pain Eye | n (%) | 1 (0.2%) | 1 (0.3%) | 0 (0.0%) | 0 (0.0%) | 2 (0.4%) |

*Each subject was counted only once per AE row or body system row, regardless of the number of occurences of the individual AE or the number of AEs within the body system.
Note:
N's reflect the number of subjects at the beginning of the time period described.

TABLE 17

INCIDENCE OF ADVERSE EVENTS CODED AS SUNBURN
(PERCENT OF SUBJECTS WITH AE)

|  | RD.06.SRE.18082 | |
|---|---|---|
|  | First Quarter | 12-month Adapelene Gel, 0.3% |
| Sunburn, All | 3.8% | 5.1% |
| Sunburn, Related to Study Drug | 2.7% | 3.1% |

Note:
The time period for study 18082 first quarter was March though August (spring and summer months).

In sum, in this study, Adapalene Gel 0.3% was well-tolerated in long-term (one-year) treatment of acne vulgaris:
Expected signs and symptoms of skin irritation (erythema, scaling, dryness and stinging/burning) were mostly mild or moderate and were transient.
Most of the AEs occurred in the first quarter, were dermatologic, and were mild or moderate in severity.
Clinical laboratory evaluations did not provide any evidence of systemic toxicity.

DISCUSSION AND OVERALL CONCLUSION

This was a multi-center, open-label study of the long-term (up to 12 months) safety of Adapalene Gel, 0.3% applied once daily in subjects with acne vulgaris. The primary objective was to assess safety and the secondary objective was to assess efficacy. Subjects were male and female (demonstrably non-gravid and either infertile or using appropriate forms of birth control), aged 12 years or older, with at least 20 to 50 inflammatory lesions (no nodules or cysts) and 20 to 100 non-inflammatory lesions. Qualified subjects (N=551) were enrolled at 20 independent centers in the United States and instructed to apply Adapalene Gel, 0.3% once daily to the face and trunk (if applicable) for a period of 12 months. Subjects were evaluated at Baseline, Week 1 and Months 1, 2, 4, 6, 8, 10 and 12 (or Early Termination Visit).

Expected signs and symptoms of local cutaneous irritation were evaluated at each visit: erythema, scaling, dryness, and stinging/burning (all rated on a scale ranging from 0 [none] to 3 [severe]). Adverse events and routine laboratory parameters (hematology, chemistry, and urinalysis) were recorded throughout the study. Efficacy data were summarized for percent changes from Baseline (in non-inflammatory, inflammatory and total lesion counts) and the Subject's assessment of acne.

Of the 551 subjects enrolled, 362 (65.7%) were treated for 3 months or more, 303 (55.0%) for 6 months or more, and 166 (30.1%) for 1 year or more. The two most frequent reasons for discontinuation were administrative actions: 93 (16.9%) subjects discontinued due to "Sponsor's decision" and 126 (22.9%) subjects discontinued due to "site closing". Fifteen (2.7%) subjects were withdrawn from the study due to an AE; 11 (2.0%) of these occurred in the first 3 months of the study. Regardless of the reason for discontinuation, data from all subjects were included in the data summaries.

Fifty point one percent of subjects were male, mean age was 18.9 years, and 72.4% were Caucasian (12.5% Black, 12.5% Hispanic, 0.5% Asian, and 2.0% Other). Most subjects had oily skin (63.9%). Skin Phototype III was the most common (35.2%).

In conclusion, Adapalene Gel, 0.3% was well-tolerated and effective in long term treatment in acne vulgaris patients. Signs and symptoms of skin irritation (erythema, dryness, scaling, and stinging/burning) were mostly mild or moderate and were transient. There were very few SAEs and none were related to study treatment. Most AEs reported in this study were of mild to moderate severity. The AE incidence by quarter showed that most AEs (including related AEs, dermatological AEs, SAEs, and AEs leading to discontinuation) occurred in the first quarter and the incidence of study drug-related AEs generally decreased over time. Nearly all of the related AEs were dermatologic.

Dry skin, skin discomfort, desquamation, erythema, pruritus and irritant dermatitis are all expected signs of irritation related to treatment with retinoids such as adapalene. The observation of drug-related sunburn was not considered clinically significant. The percentage of subjects with any sunburn during the first quarter and twelve months was low (4% and 5%, respectively) and similar to that observed during the twelve-week study about safety and efficacy of adapalene gel, 0.3% as compared to adapalene gel, 0.1% and adapalene gel, vehicle in the treatment of acne vulgaris (3% and 4% for subjects in the Adapalene Gel, 0.3% and Gel Vehicle groups, respectively). The time period for the quoted twelve-week study and the first quarter of the present study was March through August coinciding with the summer season when sunburn is expected.

All subjects contributed safety data for the treatment period with the highest incidence of adverse events and local cutaneous irritation (the first three months) including those discontinued due to the administrative actions of "Sponsor's decision" and "site closure."

Routine laboratory parameters (clinical chemistry, hematology and urinalysis) showed no evidence of systemic toxicity. No unexpected laboratory AEs occurred during the study. One subject had an AE of elevated liver enzymes considered possibly related to study drug by the Investigator. However, the subject was receiving four oral concomitant medications (citalopram, venlafaxine, alprazolam, and acetaminophen) which are metabolized via the liver. Furthermore, two of these concomitant medications (venlafaxine and acetaminophen) are known to cause increased liver function values.

Safety findings were consistent with the known profile of retinoids. No unexpected AEs, either. systemic or dermatological, or evidence of cumulative toxicity were observed over time. Consequently, extending treatment beyond 12 weeks does not suggest substantial additional risk for the subjects treated with Adapalene Gel, 0.3%.

The efficacy of Adapalene Gel, 0.3% was demonstrated for non-inflammatory, inflammatory and total lesions. Adapalene Gel, 0.3% showed continuing reductions greater than 75% in all lesion counts for subjects treated for 12 months.

In conclusion, Adapalene Gel, 0.3% was well-tolerated and effective in long-term (one-year) treatment of acne vulgaris.

- Expected signs and symptoms of skin irritation (erythema, scaling, dryness and stinging/burning) were mostly mild or moderate and were transient.
- Most of the AEs occurred in the first quarter, were dermatologic, and were mild or moderate in severity.
- Clinical laboratory evaluations did not provide any evidence of systemic toxicity.
- Continuous reductions in non-inflammatory, inflammatory, and total lesion counts occurred over time. Median reductions from baseline were greater than 75% for all lesion types by Month 12.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regimen for the treatment of acne vulgaris, comprising topically applying onto the afflicted skin area of an individual in need of such treatment, an effective amount of a topical adapalene formulation at least once every two days for a period of time of at least six months, said topical adapalene formulation comprising 0.3% adapalene by weight, wherein adapalene is the only active acne-treating agent administered during said period of time.

2. The acne vulgaris regimen as defined by claim 1, said topical adapalene formulation comprising an aqueous gel composition.

3. The acne vulgaris regimen as defined by claim 1, comprising topically applying said adapalene formulation once daily onto said afflicted skin area.

4. The acne vulgaris regimen as defined by claim 3, comprising topically applying said adapalene formulation once daily, in the evening after wash, onto said afflicted skin area.

5. The acne vulgaris regimen as defined by claim 1, comprising topically applying said adapalene formulation onto said afflicted skin area for at least nine months.

6. The acne vulgaris regimen as defined by claim 1, comprising topically applying said adapalene formulation onto said afflicted skin area for at least twelve months.

7. The acne vulgaris regimen as defined by claim 2, comprising topically applying said aqueous adapalene gel composition onto said afflicted skin area for at least nine months.

8. The acne vulgaris regimen as defined by claim 2, comprising topically applying said aqueous adapalene gel composition onto said afflicted skin area for at least twelve months.

9. The acne vulgaris regimen as defined by claim 1, said afflicted skin area containing 20 to 100 non-inflammatory lesions, 20 to 50 inflammatory lesions, and no active nodules or cysts.

* * * * *